(12) United States Patent
Takahashi et al.

(10) Patent No.: US 11,434,218 B2
(45) Date of Patent: Sep. 6, 2022

(54) POLYPHENOL PRODUCTION METHOD

(71) Applicant: NBC MESHTEC INC., Tokyo (JP)

(72) Inventors: Erika Takahashi, Tokyo (JP); Yoshie Fujimori, Tokyo (JP); Youhei Jikihara, Tokyo (JP); Tsuruo Nakayama, Tokyo (JP)

(73) Assignee: NBC MESHTEC INC., Tokyo (JP)

( * ) Notice: Subject to any disclaimer, the term of this patent is extended or adjusted under 35 U.S.C. 154(b) by 0 days.

(21) Appl. No.: 16/634,915

(22) PCT Filed: Aug. 24, 2018

(86) PCT No.: PCT/JP2018/031261
§ 371 (c)(1),
(2) Date: Jan. 29, 2020

(87) PCT Pub. No.: WO2019/044672
PCT Pub. Date: Mar. 7, 2019

(65) Prior Publication Data
US 2020/0231560 A1    Jul. 23, 2020

(30) Foreign Application Priority Data
Aug. 28, 2017  (JP) ............................. JP2017-163731

(51) Int. Cl.
*C07D 311/64*    (2006.01)
*B01J 21/04*    (2006.01)
(Continued)

(52) U.S. Cl.
CPC ............. *C07D 311/64* (2013.01); *B01J 21/04* (2013.01); *B01J 21/063* (2013.01); *B01J 21/18* (2013.01);
(Continued)

(58) Field of Classification Search
CPC ...... C07D 311/62; C07D 311/64; B01J 21/04; B01J 21/063; B01J 21/18; B01J 23/30;
(Continued)

(56) References Cited

U.S. PATENT DOCUMENTS

2009/0047305 A1   2/2009  Tanaka et al.
2009/0170928 A1   7/2009  Bruno et al.
(Continued)

FOREIGN PATENT DOCUMENTS

CN       103275053       3/2015
JP       2004-155784     6/2004
(Continued)

OTHER PUBLICATIONS

Mejias et al., "New Polymers from Natural Phenols Using Horseradish or Soybean Peroxidase", Macromol. Biosci., 2002, vol. 2, No. 1, pp. 24-32, XP-002401639.
(Continued)

*Primary Examiner* — Brian A McCaig
(74) *Attorney, Agent, or Firm* — Wenderoth, Lind & Ponack, L.L.P.

(57) ABSTRACT

[PROBLEM] To provide a novel method for synthesising a polyphenol.
[SOLUTION] A polyphenol production method including the reaction of catechin in the presence of a catalyst and an oxidising agent, said catalyst comprising a metal oxide and/or a composite that comprises: a substrate which has an inorganic material on the surface thereof; and metal nanoparticles of a particle diameter of 0.5-100 nm attached to the surface of the inorganic material.

16 Claims, 1 Drawing Sheet

(51) Int. Cl.
    *B01J 21/06*     (2006.01)
    *B01J 21/18*     (2006.01)
    *B01J 23/30*     (2006.01)
    *B01J 23/42*     (2006.01)
    *B01J 23/44*     (2006.01)
    *B01J 23/46*     (2006.01)
    *B01J 23/50*     (2006.01)
    *B01J 23/52*     (2006.01)
    *B01J 23/72*     (2006.01)
    *B01J 23/745*     (2006.01)
    *B01J 35/00*     (2006.01)

(52) U.S. Cl.
    CPC ............... *B01J 23/30* (2013.01); *B01J 23/42* (2013.01); *B01J 23/44* (2013.01); *B01J 23/462* (2013.01); *B01J 23/468* (2013.01); *B01J 23/50* (2013.01); *B01J 23/52* (2013.01); *B01J 23/72* (2013.01); *B01J 23/745* (2013.01); *B01J 35/0013* (2013.01)

(58) Field of Classification Search
    CPC ... B01J 23/42; B01J 23/44; B01J 23/46; B01J 23/462; B01J 23/468; B01J 23/50; B01J 23/52; B01J 23/72; B01J 23/745; B01J 35/0013; C07B 61/00
    See application file for complete search history.

(56) References Cited

U.S. PATENT DOCUMENTS

2009/0186125 A1*   7/2009   Colliver ................. A23F 3/163
                                                                                                      426/49

2012/0329862 A1   12/2012   Nakai et al.
2014/0031421 A1    1/2014   Dugar et al.
2017/0158660 A1*   6/2017   Fujimori ................. B01J 23/52

FOREIGN PATENT DOCUMENTS

| JP | 2010-35548 | 2/2010 |
|---|---|---|
| JP | 2010-138103 | 6/2010 |
| JP | 2011-172514 | 9/2011 |
| JP | 2012-5413 | 1/2012 |
| JP | 2017-1982 | 1/2017 |
| WO | 2005/123725 | 12/2005 |
| WO | 2006/090830 | 8/2006 |
| WO | 2006/116532 | 11/2006 |
| WO | 2012/101652 | 8/2012 |
| WO | 2015/198614 | 12/2015 |

OTHER PUBLICATIONS

Extended European Search Report dated Mar. 25, 2021 in corresponding European Patent Application No. 18850172.0.
International Preliminary Report on Patentability dated Mar. 12, 2020 in International (PCT) Patent Application No. PCT/JP2018/031261.
International Search Report (ISR) dated Nov. 20, 2018 in International (PCT) Application No. PCT/JP2018/031261.
Yue Min Chen et al., "Polymerization of catechin catalyzed by Mn-, Fe- and Al-oxides", Colloids and Surfaces B: Biointerfaces, vol. 81, No. 1, pp. 217-223, ISSN: 927-7765, 2010, cited in CA.

* cited by examiner

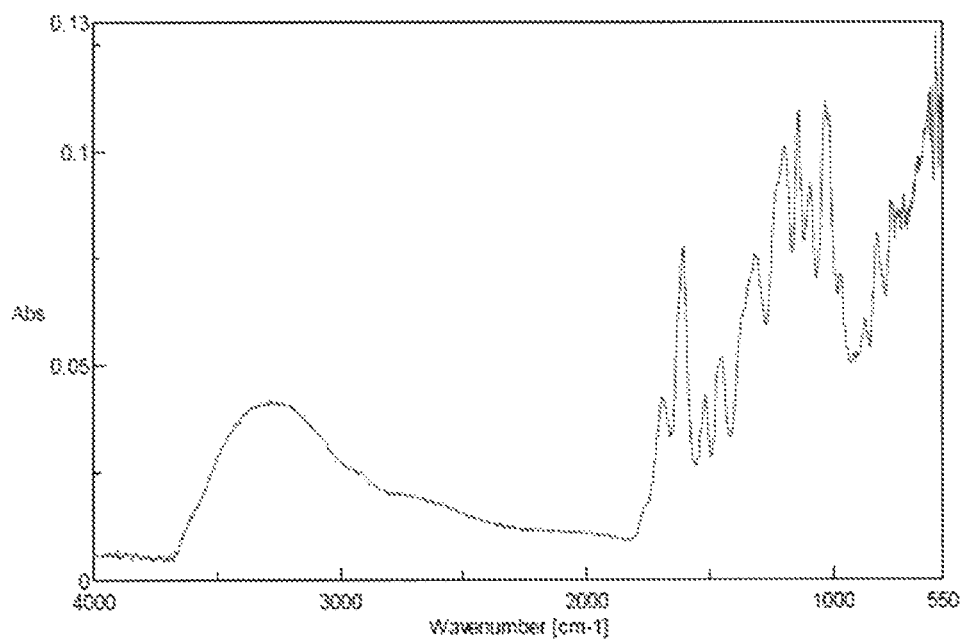

POLYPHENOL PRODUCTION METHOD

TECHNICAL FIELD

The present invention relates to a method for producing polyphenol.

BACKGROUND ART

Japanese tea, which Japanese people have been drinking for a long time, is attracting attention as one containing various functional substances. Typical substances are catechins. The presence of these catechins was confirmed for the first time in 1929 by Dr. Tsujimura et al. in Institute of Physical and Chemical Research, thereafter various functions such as antioxidant action, antibacterial action, cancer prevention and reduction of blood cholesterol concentration have been discovered, and therefore, beverages for specified health use and supplements have been commercialized.

However, production of green tea containing large amounts of catechins is limited to some areas such as Japan and China, and in about 80% of the world, fermented tea such as black tea or Oolong tea is produced. In recent years, it has become apparent that also in this fermented tea, substances called theaflavins having functions similar to those of catechins are contained, and they are attracting attention (Patent Literature 1). Furthermore, methods for synthesizing theaflavins, etc. have also been studied (Patent Literatures 2 and 3).

In addition to usefulness of catechins and theaflavins, usefulness of polyphenol having a number-average molecular weight of 9,000 to 18,000 in physiological activities such as action of suppressing fat accumulation on the liver has been found out, and a method for extracting the polyphenol from fermented tea has been disclosed (Patent Literature 4). Also, a method for producing an oligomer by condensing a catechin derivative using a Lewis acid catalyst has been disclosed (Patent Literature 5).

In addition to catechins and theaflavins, a composition of polyphenol obtained by heating an extract from a natural substance in an acid solution has also been disclosed (Patent Literature 6).

CITATION LIST

Patent Literature

Patent Literature 1
JP2004-155784
Patent Literature 2
JP2010-035548
Patent Literature 3
JP2011-172514
Patent Literature 4
JP2012-005413
Patent Literature 5
JP2017-001982
Patent Literature 6
WO 2006/090830
Patent Literature 7
WO 2015/198614

SUMMARY OF INVENTION

Technical Problem

In such methods using enzyme reaction or using cultured cells as described in Patent Literatures 2 and 3, however, there are problems such that the conditions for carrying out synthesis are extremely severe and handling is poor, or since purification such as removal of enzyme after the reaction is not easy, a complicated step such as chromatography is necessary and this is unsuitable for mass production. Regarding such extraction from a natural substance as described in Patent Literature 4, the extraction efficiency is low, and in order to enhance purity, a separation and purification step for a crude extract is necessary, resulting in a problem of a complicated production process. In the method of Patent Literature 5, catechin is not directly oligomerized, and in the preceding stage to the condensation reaction that is a step of oligomerization, a reaction to protect a hydroxyl group of catechin and a pre-process to introduce a leaving group are necessary. Also, after the condensation reaction, a post-process to remove the protective group is necessary. Accordingly, this method is a complicated method requiring a multistage process.

The composition of Patent Literature 6 is a composition in which a high-molecular substance is cleaved with an acid and thereby decreased in molecular weight, and the chemical cleavage with an acid produces substances having various molecular weights and structures, so that it is inefficient to obtain a desired substance. Moreover, it is difficult to control the decomposition reaction, and it is difficult to prepare polyphenol having desired molecular weight and structure.

The present applicant has applied a catalyst for synthesizing theaflavins and a method for synthesizing theaflavins using the catalyst (Patent Literature 7), but a method for synthesizing polyphenols other than theaflavins has not been clarified.

It is an object of the present invention to provide a novel method for synthesizing polyphenol.

Solution to Problem

That is to say, the gist of the present invention is as follows.

[1] A method for producing polyphenol comprising allowing catechins to react in the presence of an oxidizing agent and a catalyst, wherein the catalyst comprises
  a metal oxide, and/or
  a composite comprising a substrate having a surface comprising an inorganic material and metal nanoparticles adhered to a surface of the inorganic material and having a particle diameter of not less than 0.5 nm and not more than 100 nm.

[2] The method for producing polyphenol according to [1], wherein the catalyst comprises the composite, and
  the metal nanoparticles are one or more selected from the group consisting of Au, Pd, Pt, Rh, Ru, Ir, Ag, and oxides thereof.

[3] The method for producing polyphenol according to [1] or [2], wherein the catalyst comprises the composite comprising the metal nanoparticles adhered to a surface of one or more inorganic materials selected from the group consisting of $SiO_2$, $ZrO_2$, $Fe_2O_3$, $Al_2O_3$, C and $TiO_2$.

[4] The method for producing polyphenol according to any one of [1] to [3], wherein the catalyst comprises one or more metal oxides selected from the group consisting of $WO_3$, $Fe_2O_3$, $Ag_2O$ and CuO.

[5] The method for producing polyphenol according to any one of [1] to [4], wherein the oxidizing agent is hydrogen peroxide or oxygen.

[6] The method for producing polyphenol according to any one of [1] to [5], wherein in the reaction, a molar ratio between the catechin and the oxidizing agent is 1:1 to 1:50.

[7] The method for producing polyphenol according to any one of [1] to [6], wherein the reaction is carried out in a solvent and is carried out at a temperature of not lower than 15° C. and not higher than the boiling point of the solvent.

[8] The method for producing polyphenol according to [7], wherein the solvent is water.

[9] The method for producing polyphenol according to any one of [1] to [8], wherein a number-average molecular weight of the polyphenol is not less than 9,000 and not more than 18,000.

Advantageous Effect of Invention

According to the present invention, a novel method for synthesizing polyphenol can be provided.

BRIEF DESCRIPTION OF DRAWING

FIG. 1 shows an infrared absorption spectrum of polyphenol obtained in Example 19.

DESCRIPTION OF EMBODIMENT

The method for synthesizing polyphenol of the present embodiment will be described in detail hereinafter.

The present embodiment relates to a method for synthesizing polyphenol, and comprises allowing catechins to react in the presence of an oxidizing agent and a catalyst for polyphenol synthesis described later.

Polyphenol refers to a compound having a plurality of phenolic hydroxyl groups, and particularly in the present specification, it refers to a compound other than catechins, among compounds classified as polyphenols from their structures. Examples of the polyphenols according to the present embodiment include theaflavins obtained by bimolecular reaction of catechins and catechin polymers obtained by oxidative polymerization of catechins.

In the synthesis method of the present embodiment, reaction is carried out using catechins as starting materials.

The catechins are divided into pyrogallol-type catechins and catechol-type catechins. Examples of the catechol-type catechins include catechin (C), epicatechin (EC) that is a stereoisomer of catechin, and epicatechin gallate (ECg). Examples of the pyrogallol-type catechins include epigallocatechin (EGC) and epigallocatechin gallate (EGCg). In the present specification, catechins refer to compounds represented by the following general formula (I) (wherein $R^1$ is a hydrogen atom or a galloyl group) or the following general formula (II) (wherein $R^2$ is a hydrogen atom or a galloyl group). The pyrogallol-type catechin is represented by the following general formula (I), and the catechol-type catechin is represented by the following general formula (II). In the present embodiment, one of these catechins may be used as a raw material, or a mixture of two or more of them may be used as a raw material. The catechins used as raw materials may be commercial products or may be extracts from tea leaves.

[Formula 1]

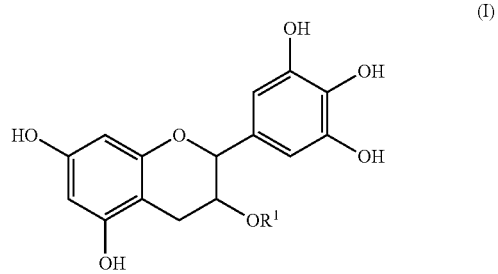

EGC: $R^1$ = H
EGCg: $R^1$ = galloyl group

[Formula 2]

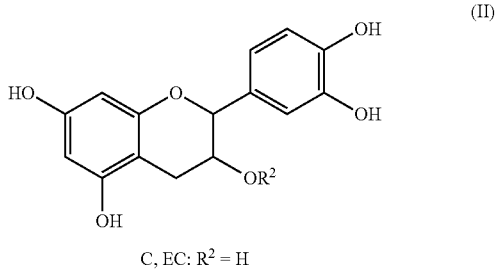

C, EC: $R^2$ = H
ECg: $R^2$ = galloyl group

In the formula (I), $R^1$ represents a hydrogen atom or a galloyl group. The epigallocatechin (EGC) is a compound of the formula (I) wherein $R^1$ is a hydrogen atom, and the epigallocatechin gallate (EGCg) is a compound of the formula (I) wherein $R^1$ is a galloyl group. In the formula (II), $R^2$ represents a hydrogen atom or a galloyl group. The catechin (C) and the epicatechin (EC) are each a compound of the formula (II) wherein $R^2$ is a hydrogen atom, and the epicatechin gallate (ECg) is a compound of the formula (II) wherein $R^2$ is a galloyl group.

In the present embodiment, the reaction can be carried out in, for example, a solution.

The solvent for use in the synthesis reaction is not particularly limited as long as it can dissolve catechins, and solvents known to a person skilled in the art, such as water, methanol, ethanol, 1-propanol, 2-propanol, 1-butanol, formic acid, acetic acid phosphoric acid, acetone, methyl ethyl ketone, methyl isobutyl ketone, acetonitrile, dichloromethane, N,N-dimethylformamide, dimethyl sulfoxide and ethyl acetate, can be used singly or as a mixture of two or more. Water is preferable as a reaction solvent because it has high safety and can often dissolve also polyphenol that is a product.

Next, the catalyst for polyphenol synthesis used in the present embodiment will be described. The catalyst for polyphenol synthesis according to the present embodiment comprises a metal oxide and/or a composite. The composite comprises a substrate having a surface comprising an inorganic material and metal nanoparticles adhered to a surface of the inorganic material and having a particle diameter of not less than 0.5 nm and not more than 100 nm. In the composite, the metal nanoparticles are adhered to the inorganic material of the substrate surface, whereby the composite has extremely high oxidation catalyst ability. The metal nanoparticles can be adhered to the inorganic material by various methods described later.

The substrate of the composite employable in the present embodiment is not particularly limited as long as it has a surface comprising an inorganic material. Specific examples of the substrates include a substrate having a surface composed of an inorganic material and a substrate the whole of which is composed of an inorganic material.

The inorganic material can be constituted of one or more of zeolite, apatite, carbon materials such as activated carbon, diatomaceous earth, metal oxides, etc. The inorganic material is preferably constituted of a metal oxide among them.

Examples of methods to form the substrate having a surface comprising a metal oxide include, but are not particularly limited to, a method of electrochemically forming a thin film of a metal oxide film by anodic oxidation, a method of oxidizing a metal surface by heat treatment, and a method of forming an oxide thin film through sputtering or ion plating. The whole of the substrate may be composed of a metal oxide.

By constituting the inorganic material from a metal oxide, exchange of oxygen molecules is actively carried out, and therefore, catalytic activity can be further enhanced. As the metal oxides, oxides of silicon, zirconium, zinc, titanium, chromium, iron, copper, tin, aluminum and the like are preferable, and for example, the inorganic material may be constituted of one or more of these metal oxides. In particular, the inorganic material is more preferably constituted of one or more of $SiO_2$, $ZrO_2$, $Fe_2O_3$, $Al_2O_3$, C and $TiO_2$ because catalytic activity is still further enhanced from the viewpoint of relation to the amount of the aforesaid metal nanoparticles adhered, and the inorganic material is still more preferably constituted of one or more of $SiO_2$, $Fe_2O_3$, $Al_2O_3$ and $TiO_2$.

It is preferable to select, as the metal nanoparticles according to the present embodiment, one or more from the group consisting of, for example, gold (Au), silver (Ag), palladium (Pd), platinum (Pt), rhodium (Rh), iridium (Ir), ruthenium (Ru), and oxides thereof because productivity of polyphenol can be enhanced. For the same reason, it is more preferable to use, as the metal nanoparticles according to the present embodiment, one or more selected from the group consisting of gold, palladium, platinum, rhodium and iridium.

In the present specification, the metal nanoparticles refers to metal particles having a particle diameter of less than 1 μm.

In the present embodiment, the average particle diameter of the metal nanoparticles is preferably not less than 0.5 nm and not more than 100 nm, more preferably not less than 0.5 nm and not more than 20 nm, still more preferably not less than 0.5 nm and not more than 10 nm. Metal nanoparticles having an average particle diameter of less than 0.5 nm tend to become, as a substance, more unstable than those having an average particle diameter of not less than 0.5 nm, and metal nanoparticles having an average particle diameter of more than 100 nm are decreased in catalytic activity as compared with metal nanoparticles having an average particle diameter of not more than 100 nm. On the other hand, by setting the average particle diameter to not more than 100 nm (more preferably not more than 20 nm, still more preferably not more than 10 nm), the catalytic activity is further enhanced.

The average particle diameter referred to in the present specification is an average value of particle diameters of not less than 300 metal nanoparticles actually measured on a TEM image.

Control of the particle diameter can be carried out by, for example, controlling pH of the solution in the preparation of metal nanoparticles based on a known method.

A method for adhering the metal nanoparticles to the inorganic material of the substrate is not particularly limited, and can be appropriately set. For example, the metal nanoparticles may be adhered to the inorganic material of the substrate surface by means of a binder, drying by heating, or the like.

Furthermore, the metal nanoparticles may be adhered to the inorganic material by applying colloids to the inorganic material portion of the substrate surface and drying them.

For example, when palladium or palladium oxide is adhered to the inorganic material, palladium ions may be adsorbed by the inorganic material through a chemical method such as zeta potential or diffusion of palladium ions to adhere palladium or palladium oxide to the inorganic material. Furthermore, nanoparticles of palladium or palladium oxide may be adhered to the inorganic material by immersing a substrate having a surface comprising the inorganic material in an aqueous solution containing palladium ions to perform coating and then immersing the substrate in an aqueous solution containing a reducing agent such as an organic acid, formaldehyde or hydrazine or subjecting the substrate to reduction treatment in a hydrogen reducing atmosphere.

Moreover, for example, metal nanoparticles having a semispherical shape or the like may be closely bonded to the inorganic material, and by virtue of this bonding, a bonded interface perimeter may be formed in the inorganic material. In this case, the metal nanoparticles are directly bonded to the inorganic material utilizing a difference in zeta potential between the inorganic material and the metal nanoparticles. The bonding referred to in the present specification means that the inorganic material and the metal nanoparticles are in contact with each other at the interface (bonded interface) and are adhered to each other, while the bonded interface perimeter refers to a perimeter of the bonded interface. In the present specification, the direct bonding means that the inorganic material of the substrate surface and the metal nanoparticles are adhered to each other without any other material such as a binder between them.

The metal nanoparticles are directly bonded to the inorganic material of the substrate surface, the bonded interface perimeter is present in a state of being exposed on the surface of the catalyst, and the catalyst having the bonded interface perimeter between the substrate and the metal nanoparticles acts on catechin, whereby the polyphenol synthesis reaction further proceeds. To specifically describe this point, oxygen defects are easily formed in the bonded interface perimeter, and it is presumed that activation of oxygen molecules or hydrogen molecules proceeds here. Accordingly, in order to enhance oxidative catalytic activity or selectivity, the presence of this bonded interface perimeter is advantageous. On that account, the present embodiment preferably has the bonded interface perimeter formed by bonding of the metal nanoparticles and the inorganic material to each other.

The method to adhere the metal nanoparticles to the inorganic material surface in a state where the bonded interface perimeter has been formed by the direct bonding is not particularly limited. Specific examples thereof include co-precipitation method, impregnation method, sol-gel method, dropping neutralization precipitation method, reducing agent addition method, pH control neutralization precipitation method, metal carboxylate addition method, colloidal method, deposition precipitation method (DP method), urea method, deposition reduction method, solid phase mixing method (SG method) and co-precipitation method (One-pot method), and these methods can be appropriately used according to the type of the inorganic material of the substrate surface.

A method for preparing the catalyst for polyphenol synthesis of the present embodiment using a gold compound will be specifically described hereinafter taking the deposition precipitation method as an example. In a specific method of deposition precipitation, first, an aqueous solution in which a gold compound is dissolved is heated to 20 to 90° C., preferably 50 to 70° C., and while stirring, pH of the solution is adjusted to 3 to 10, preferably 5 to 8, with an alkali solution. Thereafter, to the solution, an inorganic material that becomes the substrate is added, then the resulting mixture is further stirred at 50 to 70° C., and then the mixture is filtered and calcined, whereby the catalyst for polyphenol synthesis of the present embodiment can be obtained.

Examples of the gold compounds employable for the preparation of the gold compound aqueous solution include $HAuCl_4 \cdot 4H_2O$, $NH_4AuCl_4$, $KAuCl_4 \cdot nH_2O$, $KAu(CN)_4$, $Na_2AuCl_4$, $KAuBr_4 \cdot 2H_2O$ and $NaAuBr_4$. Although a concentration of the gold compound in the gold compound aqueous solution is not particularly limited, it is preferably $1 \times 10^{-1}$ to $1 \times 10^{-5}$ mol/L.

The amount of the metal nanoparticles supported on the inorganic material is not particularly limited, but it is preferably 0.5 to 30 mass %, more preferably 0.5 to 25 mass %, based on the inorganic material. The reason why the amount of 0.5 to 25 mass % is more preferable is that if the metal nanoparticles are supported in a ratio of more than 25 mass %, the metal nanoparticles are easily aggregated to one another, and the oxidation reduction action is decreased as compared with a case where the amount thereof is in the above range.

In the aforesaid composite, the metal nanoparticles are adhered to the inorganic material of the substrate surface, and besides, oxide particles of, for example, titanium, aluminum or iron may be further supported thereon. A method for allowing the inorganic material surface to support the oxide particles is not particularly limited, and for example, the oxide particles may be supported on the inorganic material by thermal spraying method. The oxide particles supported on the inorganic material can suppress adhesion of a substance, which inhibits catalytic activity of the metal nanoparticles, to the metal nanoparticles, oxidation reduction action can be stably continued over a longer period of time.

The catalyst for polyphenol synthesis may have a metal oxide instead of the composite or together with the composite.

The metal oxide that can be used is not particularly limited as long as it has oxidation catalyst ability, and preferred examples thereof include $Al_2O_3$, $Ag_2O$, $CeO_2$, $CuO$, $Cu_2O$, $Fe_2O_3$, $MnO_2$, $MoO_3$, $V_2O_5$ and $WO_3$. Particularly in the case of $Ag_2O$, $Fe_2O_3$, $WO_3$ and $CuO$, the yield of polyphenol is further increased, so that the metal oxide is more preferably constituted of at least one of them, and is still more preferably constituted of $Ag_2O$ and/or $WO_3$. Although the shape of the metal oxide is not particularly limited, it is preferably particulate because the specific surface area is increased, and the catalytic activity is enhanced. The metal oxide may be fixed to the substrate.

As the catalyst for polyphenol synthesis, the above metal oxides may be used singly or may be used as a mixture of two or more. Furthermore, the metal oxide and the aforesaid composite may be used in combination.

The catalyst for polyphenol synthesis according to the present embodiment can have various shapes. A method for controlling the shape is not particularly limited and can be appropriately set by a person skilled in the art. When the catalyst for polyphenol synthesis has the aforesaid composite, the catalyst can be molded into an arbitrary shape by, for example, controlling the shape of the substrate. For example, the catalyst for polyphenol synthesis of the present embodiment can be made to have a shape of a powder, a granule, a tablet obtained by pressure molding, or the like. Moreover, by using, as the substrate, a woven or knitted fabric, a nonwoven fabric or a sheet, each being formed of a fibrous inorganic material, or by using, as the substrate, a foil-like or plate-like metal oxide or the like, the catalyst for polyphenol synthesis of the present embodiment can be made to have a shape of a filter, a sheet or the like.

When the catalyst for polyphenol synthesis of the present embodiment has a shape of aforesaid powder, granule or tablet obtained by pressure molding, an embodiment in which the catalyst is included in a fibrous structure or fixed to an outer surface of a fibrous structure can be given.

Specific treatment to make the fibrous structure include the catalyst for polyphenol synthesis of the present embodiment or to fix the catalyst to the fibrous structure is not particularly limited and can be appropriately selected by a person skilled in the art. For example, the catalyst for polyphenol synthesis of the present embodiment may be included in the fibrous structure by adding the catalyst to the polymer material, then kneading the mixture and spinning it. Furthermore, the catalyst for polyphenol synthesis may be fixed to the fibrous structure such as a woven fabric or a nonwoven fabric using a binder, a coupling agent or the like. Moreover, the catalyst for polyphenol synthesis is fixed to an inorganic material such as zeolite, and then the inorganic material with the catalyst for polyphenol synthesis fixed thereto is fixed to the fibrous structure, whereby a catalyst filter for polyphenol synthesis is produced, or after the substrate composed of, for example, inorganic oxide particles is fixed to a fibrous base, the substrate is immersed in a hydrate in which a material of metal nanoparticles is dissolved, whereby the metal nanoparticles can be deposited on the surfaces of the inorganic oxide particles or the like.

In the present specification, the concept of inclusion of the catalyst for polyphenol synthesis also includes a case where the catalyst for polyphenol synthesis is exposed outside the fibrous structure.

The binder component is not particularly limited, and can be appropriately selected taking adhesion to the fibrous base, etc. into consideration. For example, as synthetic resins, polyester resins, amino resins, epoxy resins, polyurethane resins, acrylic resins, water-soluble resins, vinyl-based resins, fluorine resins, silicone resins, cellulose-based resins, phenol resins, xylene resins, toluene resins, etc. can be used. As natural resins, drying oils such as castor oil, linseed oil and tung oil can be used.

In the fixing of the catalyst for polyphenol synthesis of the present invention to the fibrous base, the catalyst may be fixed thereto using the binder or the like. Alternatively, fixing may be carried out by dispersing the catalyst for polyphenol synthesis of the present embodiment to which a silane monomer having an unsaturated bond has been chemically bonded through reflux treatment or the like, in a solvent such as methanol, coating the fibrous base with the resulting dispersion or immersing it in the dispersion, then irradiating it with a radiation such as electron ray, and performing chemical bonding through graft polymerization.

Some examples of the silane monomers used include vinyltrichlorosilane, vinyltrimethoxysilane, vinyltriethoxysilane, vinyltriacetoxysilane, N-β-(N-vinylbenzylaminoethyl)-γ-aminopropyltrimethoxysilane, hydrochloride of N-(vinylbenzyl)-2-aminoethyl-3-aminopropyltrimethoxysilane, 2-(3,4-epoxycyclohexyl)ethyltrimethoxysilane, 3-glycidoxypropyltrimethoxysilane, 3-glycidoxypropylmethyldiethoxysilane, 3-glycidoxypropyltriethoxysilane, p-styryltrimethoxysilane, 3-methacyryloxypropylmethyldimethoxysilane, 3-methacryloxypropyltrimethoxysilane, 3-methacryloxypropylmethyldiethoxysilane, 3-methacryloxypropyltriethoxysilane, 3-acryloxypropyltrimethoxysilane, 3-isocyanatopropyltriethoxysilane, bis(triethoxysilylpropyl)tetrasulfide, 3-aminopropyltrimethoxysilane, 3-aminopropyltriethoxysilane, 3-triethoxysilyl-N-(1,3-dimethyl-butylidene)propylamine, N-phenyl-3-aminopropyltrimethoxysilane, N-2-(aminoethyl)-3-aminopropylmethyldimethoxysilane, N-2-(aminoethyl)-3-aminopropyltrimethoxysilane, N-2-(aminoethyl)-3-aminopropyltriethoxysilane, 3-mercaptopropylmethyldimethoxysilane, 3-mercaptopropyltrimethoxysialne, N-phenyl-3-aminopropyltrimethoxysilane, special aminosilane, 3-ureidopropyltriethoxysilane, 3-chloropropyltrimethoxysilane, tetramethoxysilane, tetraethoxysilane, methyltrimethoxysilane, methyltriethoxysilane, dimethyldiethoxysilane, phenyltriethoxysilane, hexamethyldisilazane, hexyltrimethoxysilane, decyltrimethoxysilane, hydrolyzable group-containing siloxane, fluoroalkyl group-containing oligomer, methyl hydrogen siloxane, and silicone quaternary ammonium salt.

A specific example of the method for producing the fibrous structure is a method in which when a nonwoven fabric produced by entangling fibers, a mixed paper produced by mixing pulp and a binder, or the like is produced as the base, the catalyst for polyphenol synthesis of the present embodiment is mixed, and by virtue of this method, the catalyst can be held within spaces inside the base. The catalyst for polyphenol synthesis of the present embodiment may be fixed by discharging a thermoplastic resin, a reactive hot-melt adhesive or a resin that is reactive-cured by particle beams such as ultraviolet ray and electron ray, into fibers through a nozzle, bringing the catalyst for polyphenol synthesis of the present embodiment into contact with the thus discharged fibers while the surfaces of the fibers have tackiness, and then performing curing reaction treatment. This fixing can be carried out by retuning the temperature of the hot-melt adhesive to room temperature to thereby adhere the catalyst, or by reactive-curing the reactive hot-melt adhesive with moisture in the air, or by irradiating the resin, which is crosslinked by ultraviolet ray or electron ray, with ultraviolet ray or electron ray to perform curing reaction.

Examples of resins used as above include hot-melt adhesives containing, as main components, resins such as low-density polyethylene, linear low-density polyethylene, polypropylene, an ethylene/vinyl acetate copolymer resin, an ethylene/methyl methacrylate copolymer resin and an ethylene/ethyl acrylate copolymer resin, reactive hot-melt adhesives having urethane polymers as main bodies, and resins that contain polyurethane acrylate and/or polyester resins as main components and are crosslinked by ultraviolet ray or electron ray.

Next, the process for producing polyphenol will be described by giving an example.

First, a catechin that is a raw material is added to a solvent, stirred and dissolved to obtain a solution (referred to as a catechin solution hereinafter). The concentration of the catechin in the catechin solution is not particularly limited and can be appropriately set by a person skilled in the art, but a ratio between the concentration of the metal nanoparticles supported on the catalyst for polyphenol synthesis (μmol/mL) and/or the concentration of the metal oxide (μmol/mL) and the total catechin concentration (μmol/mL) is preferably 1:1 or more because the yield of polyphenol can be enhanced. The upper limit of the ratio between the concentration of the metal nanoparticles (μmol/mL) and/or the concentration of the metal oxide (μmol/mL) and the total catechin concentration (μmol/mL) is not particularly limited, but if the ratio of the catechin concentration to the catalyst concentration is high, the reaction rate decreases, so that from the viewpoint of productivity, the ratio is preferably 1:1000 or less. When water is used as a solvent, catechin exists stably, and therefore, water may be used in an acid state. In order to enhance solubility of catechins, alcohols such as ethanol may be added to the catechin solution.

As the oxidizing agents for use in the reaction of the present embodiment, oxidizing agents known to a person skilled in the art, for example, permanganic acids such as sodium permanganate, potassium permanganate, zinc permanganate, calcium permanganate and magnesium permanganate, dichromates such as potassium dichromate, chloromates such as potassium chromate, persulfates such as ammonium persulfate, sodium persulfate and potassium persulfate, dilute nitric acid, oxygen gas, ozone, and hydrogen peroxide can be used. Of these, oxygen gas and hydrogen peroxide are preferable because they are easy to handle. Oxygen gas can be easily supplied to the catechin solution by bubbling. Hydrogen peroxide can be dissolved in the catechin solution prior to the reaction. Even when oxygen gas and hydrogen peroxide remain in an unreacted state after completion of the reaction, they can be easily decomposed and removed by an operation of pressure reduction or heating, or natural volatilization, so that there is an advantage that they hardly remain as impurities in the resulting polyphenol.

In the reaction of the present embodiment, for example, the aforesaid catalyst for polyphenol synthesis and oxidizing agent are added to the aforesaid catechin solution to promote the reaction.

Regarding the amount of the oxidizing agent used in the reaction of the present embodiment, the molar ratio between the catechin and the oxidizing agent is preferably 1:1 to 1:200, more preferably 1:1 to 1:50.

If the proportion of the oxidizing agent is lower than that in the molar ratio of 1:1, the reaction does not easily proceed as compared with the case where the proportion thereof is in the above range, so that the molecular weight of the polyphenol produced is low, and a large amount of unreacted catechin remains.

There is not much difference in the molecular weight of polyphenol obtained when other reaction conditions are the same between a case where the proportion of the oxidizing agent is higher than that in the molar ratio of 1:50 and a case where the proportion of the oxidizing agent is lower than that in the molar ratio of 1:50, and this difference further decreases in the case where the proportion of the oxidizing agent is higher than that in the molar ratio of 1:200 and the case where the proportion of the oxidizing agent is the same as or lower than that in the molar ratio of 1:200. On that account, there is less need to use the oxidizing agent in an amount larger than that in the case of the molar ratio of 1:200.

The reaction temperature is not particularly limited as long as the solution exists as a liquid, but it is preferably not lower than 4° C. and not higher than the boiling point of the solvent, more preferably not lower than 15° C., at which the reaction efficiency of the catalyst is further enhanced, and not higher than the boiling point of the solvent. As the reaction temperature rises, the reaction rate increases, but the reaction at temperatures of not lower than the boiling point of the solvent needs a pressure vessel and the reaction apparatus becomes complicated, so that such temperatures are undesirable.

The reaction is carried out, for example, while stirring, and when a certain time is reached, the reaction can be terminated by a method of removing the catalyst, or the like. Since the molecular weight increases with the reaction time, the reaction time only needs to be controlled according to the desired molecular weight.

The polyphenol produced by the reaction of the present embodiment is not particularly limited, but from the viewpoint of further enhancement of physiological activities, polyphenol having a number-average molecular weight of not less than 3,000 and not more than 20,000 is preferable. Polyphenol having a number-average molecular weight of not less than 9,000 and not more than 18,000 is more preferable because physiological activities are still further enhanced.

Examples of the physiological activities include an action of suppressing fat accumulation on the liver described in Patent Literature 4 and antioxidant activity.

In the present embodiment, whether the reaction has proceeded or not can be confirmed by measuring a molecular weight of the product and detecting that the product has a plurality of phenolic hydroxyl groups in its structure.

The molecular weight of the product can be measured by gel permeation chromatography or usual instrumental analysis such as GPC-MALS method or MALDI-TOFMS method. For example, in the examples described later, the number-average molecular weight of polyphenol that is a product is represented by a molecular weight in terms of polystyrene based on gel permeation chromatography under the following conditions.

Column: TSKgel α-3000 (Tosoh Corporation)
Eluent: 10 mM lithium chloride-containing dimethylformamide
Flow rate: 0.6 ml/min
Temperature: 40° C.
Detector: UV detector (measurement wavelength: 275 nm)

Whether the product has a plurality of phenolic hydroxyl groups or not can be detected by, for example, infrared absorption spectrum measurement or absorbance measurement by Folin-Ciocalteu method. Furthermore, by carrying out further identification of the molecular structure of the resulting compound by, for example, a known method, it may be confirmed that the compound has a plurality of phenolic hydroxyl groups.

After the reaction is completed, a suspension containing the resulting polyphenol and the catalyst for polyphenol synthesis is subjected to centrifugation, filtration using a filter, or the like to remove the catalyst for polyphenol synthesis, whereby a solution containing polyphenol (referred to as a polyphenol solution hereinafter) is obtained.

The resulting polyphenol solution may be utilized as it is, or polyphenol may be isolated and recovered by removing the solvent from the polyphenol solution through evaporation, reprecipitation or the like.

When necessary, low-molecular components such as unreacted catechin may be removed or components having particularly high activity may be extracted, by a method of dialysis, chromatography or the like.

The catalyst for polyphenol synthesis separated by centrifugation or the like can be repeatedly subjected to synthesis of polyphenol.

As described hereinbefore, in the present embodiment, the catalyst can be easily removed from the product by a method of filtration or the like after production of polyphenol, and the process is simple, differently from the case of carrying out the reaction using enzyme or the like. In the case of carrying out the reaction using an enzyme or the like, polyphenol cannot be efficiently synthesized unless special conditions such as temperature and pH are adopted, but in the present embodiment, the reaction can be efficiently carried out under a wider range of conditions. On that account, by selecting the staring materials and the reaction conditions, polyphenols having various structures and molecular weights can be produced. In the conventional chemical synthesis method, an organic solvent is necessary, and pretreatment such as introduction of a protective group into catechin is sometimes necessary, but the method of the present embodiment is an easy and safe production method in which the reaction can be carried out even in a water solvent having a low environmental burden and any treatment is not needed before and after the reaction.

EXAMPLES

Next, the present invention will be described more specifically with reference to the examples. However, the present invention is in no way limited to those examples only.

Preparation of catalyst for polyphenol synthesis (Preparation Example 1): Pd

A palladium chloride aqueous solution was weighed in such a manner that the amount of palladium supported became 1 wt % based on a substrate, then the solution was dissolved in 1.5 mL of distilled water, and to the resulting solution, 50 μL of ethylene glycol was added, thereby preparing a complex solution. As the substrate, 1 g of a titanium oxide powder was weighed, and 1.5 mL of distilled water was added to the powder to suspend the powder. Subsequently, while stirring, the complex solution was added to the suspension of the titanium oxide powder as the substrate, and the resulting mixture was dried with a dryer at 60° C. until there was no moisture left, thereby powdering the mixture. This dry powder was calcined at 250° C. for one hour and pulverized to obtain a palladium nanoparticle-supported catalyst for polyphenol synthesis. The particle diameter of the palladium nanoparticle supported was 12.5 nm.

(Preparation Example 2): Ir

An iridium nanoparticle-supported catalyst for polyphenol synthesis was obtained in the same manner as in Preparation Example 1, except that palladium chloride was changed to iridium chloride. The particle diameter of the iridium nanoparticle supported was 5.7 nm.

(Preparation Example 3): Ag

A silver nanoparticle-supported catalyst for polyphenol synthesis was obtained in the same manner as in Preparation Example 1, except that palladium chloride was changed to silver nitrate. The particle diameter of the silver nanoparticle supported was 9.8 nm.

(Preparation Example 4): Pt

A platinum nanoparticle-supported catalyst for polyphenol synthesis was obtained in the same manner as in Preparation Example 1, except that palladium chloride was changed to chloroplatinic acid and the substrate was changed to silicon oxide. The particle diameter of the platinum nanoparticle supported was 6.8 nm.

(Preparation Example 5): Au

In 100 mL of water, a 0.5 mmol chloroauric acid aqueous solution was dissolved, then the resulting solution was heated to 70° C., and pH of the solution was adjusted to 7.0 with a NaOH aqueous solution. To the aqueous solution, 1 g of a titanium oxide powder was added as a substrate, and the mixture was stirred for one hour. Thereafter, the mixture was subjected to solid-liquid separation, then vacuum dried, calcined at 300° C. for 4 hours and pulverized to obtain a gold nanoparticle-supported catalyst for polyphenol synthesis. The particle diameter of the gold nanoparticle supported was 1.8 nm.

Synthesis of Polyphenol

Example 1

As raw materials, epicatechin (EC) and epigallocatechin (EGC) were each added to pure water in such a manner that the amount of each of them became 3.2 mM, and dissolved therein to obtain catechin aqueous solutions. In a 5 mL tube, the resulting catechin aqueous solutions were placed in each amount of 2 mL, and thereto was added 100 μL of a 3% hydrogen peroxide solution, thereby preparing a reaction solution. The molar ratio between the catechins and hydrogen peroxide was set to 1:25. Then, 13 mg of the palladium nanoparticle-supported catalyst prepared in Preparation Example 1 was weighed and added to the reaction solution, and the mixture was stirred overnight. After the reaction was completed, the reaction solution was made to pass through a filtration filter having a pore diameter of 0.45 μm to remove the catalyst, and subsequently, water was removed by evaporation, thereby obtaining polyphenol.

Example 2

Polyphenol was obtained by changing the catalyst to the iridium nanoparticle-supported catalyst prepared in Preparation Example 2 and allowing the reaction to proceed in the same manner as in Example 1.

Example 3

Polyphenol was obtained by changing the catalyst to the silver nanoparticle-supported catalyst prepared in Preparation Example 3 and allowing the reaction to proceed in the same manner as in Example 1.

Example 4

Polyphenol was obtained by changing the catalyst to the platinum nanoparticle-supported catalyst prepared in Preparation Example 4 and allowing the reaction to proceed in the same manner as in Example 1.

Example 5

Polyphenol was obtained by changing the catalyst to the gold nanoparticle-supported catalyst prepared in Preparation Example 5 and allowing the reaction to proceed in the same manner as in Example 1.

Example 6

Polyphenol was obtained by changing the catalyst to a commercially available 1% gold-supported iron oxide catalyst (Haruta Gold Inc.) and allowing the reaction to proceed in the same manner as in Example 1.

Example 7

Polyphenol was obtained by changing the catalyst to a commercially available 1% gold-supported carbon (Ketjen black) catalyst (Haruta Gold Inc.) and allowing the reaction to proceed in the same manner as in Example 1.

Example 8

Polyphenol was obtained by changing the catalyst to a commercially available 5% rhodium-supported alumina catalyst (Wako Pure Chemical Industries, Ltd.) and allowing the reaction to proceed in the same manner as in Example 1.

Example 9

Polyphenol was obtained by changing the catalyst to a commercially available 0.5% ruthenium-supported alumina catalyst (N.E. CHEMCAT Corporation) and allowing the reaction to proceed in the same manner as in Example 1.

Example 10

Polyphenol was obtained by changing the catalyst to commercially available silver oxide (Wako Pure Chemical Industries, Ltd.) and allowing the reaction to proceed in the same manner as in Example 1.

Example 11

Polyphenol was obtained by changing the catalyst to commercially available copper oxide (Wako Pure Chemical Industries, Ltd.) and allowing the reaction to proceed in the same manner as in Example 1.

Example 12

Polyphenol was obtained by changing the catalyst to commercially available tungsten oxide (JUNSEI CHEMICAL CO. LTD.) and allowing the reaction to proceed in the same manner as in Example 1.

Example 13

Polyphenol was obtained by changing the catalyst to commercially available iron oxide (Haruta Gold Inc.) and allowing the reaction to proceed in the same manner as in Example 1.

Example 14

Polyphenol was obtained by allowing the reaction to proceed in the same manner as in Example 5, except that the catechins as the raw materials were changed to epicatechin (EC) only.

Example 15

Polyphenol was obtained by allowing the reaction to proceed in the same manner as in Example 5, except that the catechins as the raw materials were changed to epigallocatechin (ECG) only.

Example 16

Polyphenol was obtained by allowing the reaction to proceed in the same manner as in Example 5, except that the catechins as the raw materials were changed to epicatechin gallate (ECg) only.

Example 17

Polyphenol was obtained by allowing the reaction to proceed in the same manner as in Example 5, except that the catechins as the raw materials were changed to epigallocatechin gallate (EGCg) only.

Example 18

Polyphenol was obtained by allowing the reaction to proceed in the same manner as in Example 5, except that the catechins as the raw materials were changed to catechin (C) only.

Example 19

As a raw material, epigallocatechin gallate (EGCg) was added to pure water in such a manner that the amount thereof became 156 mM, and dissolved therein to obtain a catechin aqueous solution. In a 5 mL tube, 2 mL of the resulting catechin aqueous solution was placed, and thereto was added 50 µL of a 30% hydrogen peroxide solution, thereby preparing a reaction solution.

The molar ratio between the catechin and hydrogen peroxide was set to 1:5.2. Then, 66 mg of the gold nanoparticle-supported catalyst prepared in the preparation example was weighed and added to the reaction solution, and the mixture was stirred at 60° C. for 0.5 hour. After the reaction was completed, the reaction solution was made to pass through a filtration filter having a pore diameter of 0.45 µm to remove the catalyst, and subsequently, water was removed by evaporation, thereby obtaining polyphenol.

Example 20

Polyphenol was obtained by allowing the reaction to proceed in the same manner as in Example 19, except that the reaction time was changed to one hour.

Example 21

Polyphenol was obtained by allowing the reaction to proceed in the same manner as in Example 19, except that the reaction time was changed to 24 hours.

Example 22

Polyphenol was obtained by allowing the reaction to proceed in the same manner as in Example 19, except that the amount of the 30% hydrogen peroxide solution added was changed to 100 µL (the molar ratio between the catechin and hydrogen peroxide was 1:10.4).

Example 23

Polyphenol was obtained by allowing the reaction to proceed in the same manner as in Example 19, except that the amount of the 30% hydrogen peroxide solution added was changed to 25 µL (the molar ratio between the catechin and hydrogen peroxide was 1:2.6), and the reaction time was changed to one hour.

Comparative Example 1

Polyphenol was obtained by changing the catalyst to commercially available silicon oxide (Haruta Gold Inc.) and allowing the reaction to proceed in the same manner as in Example 1. [0073]

Comparative Example 2

Polyphenol was obtained by allowing the reaction to proceed in the same manner as in Example 1, except that the catalyst was not added.

Comparative Example 3

Polyphenol was obtained by allowing the reaction to proceed in the same manner as in Example 19, except that hydrogen peroxide was not added.

Confirmation of Possession of a Plurality of Phenolic Hydroxyl Groups and Molecular Weight Measurement (Confirmation of Production of Polyphenol))

It was confirmed as below that the product was polyphenol.

The products of the examples and the comparative examples were each subjected to infrared absorption spectrum measurement for checking presence or absence of a peak showing a hydroxyl group (3500 to 3200 cm$^{-1}$) and absorbance measurement (wavelength: 765 nm) by Folin-Ciocalteu method based on ISO 14502-1:2005, thereby confirming that the products had a plurality of phenolic hydroxyl groups.

In FIG. 1, an infrared absorption spectrum of polyphenol obtained in Example 19 is given as an example.

Moreover, the products were subjected to gel permeation chromatography (GPC) to analyze them, and the amounts of the products were calculated. The molecular weight of each of the products was set to not less than 3,000 in terms of polystyrene. The amount of each of the products is expressed in terms of a ratio of the area of the product component to the total peak area in GPC. At the same time, the number-average molecular weights of the products were calculated.

As the column, TSKgel α-3000 (Tosoh Corporation) was used, and the molecular weight was calculated using standard polystyrene. The detection wavelength was set to 275 nm.

The results of the amounts and the number-average molecular weights of the products are set forth in Table 1. As shown in Table 1, production of polyphenol was confirmed in Examples 1 to 23, but in Comparative Examples 1 to 3, production of polyphenol was hardly able to be confirmed.

TABLE 1

| | Raw material | Metal Species | Sub-strate | Raw material: oxidizing agent molar ratio | Reaction temperature | Reaction time | Polyphenol area ratio (%) | Number-average molecular weight |
|---|---|---|---|---|---|---|---|---|
| Example 1 | EC + EGC | Pd | $TiO_2$ | 1:25 | Room temperature | Overnight | 83.3 | 10,400 |
| Example 2 | EC + EGC | Ir | $TiO_2$ | 1:25 | Room temperature | Overnight | 70.4 | 9,430 |
| Example 3 | EC + EGC | Ag | $TiO_2$ | 1:25 | Room temperature | Overnight | 23.8 | 3,540 |
| Example 4 | EC + EGC | Pt | $SiO_2$ | 1:25 | Room temperature | Overnight | 39.7 | 5,050 |
| Example 5 | EC + EGC | Au | $TiO_2$ | 1:25 | Room temperature | Overnight | 59.3 | 38,500 |
| Example 6 | EC + EGC | Au | $Fe_2O_3$ | 1:25 | Room temperature | Overnight | 63.1 | 31,400 |
| Example 7 | EC + EGC | Au | C | 1:25 | Room temperature | Overnight | 55.0 | 35,300 |
| Example 8 | EC + EGC | Rh | $Al_2O_3$ | 1:25 | Room temperature | Overnight | 65.0 | 24,600 |
| Example 9 | EC + EGC | Ru | $Al_2O_3$ | 1:25 | Room temperature | Overnight | 40.8 | 9,540 |
| Example 10 | EC + EGC | $Ag_2O$ | | 1:25 | Room temperature | Overnight | 65.4 | 42,300 |
| Example 11 | EC + EGC | CuO | | 1:25 | Room temperature | Overnight | 50.5 | 14,500 |
| Example 12 | EC + EGC | $WO_3$ | | 1:25 | Room temperature | Overnight | 69.9 | 41,500 |
| Example 13 | EC + EGC | $Fe_2O_3$ | | 1:25 | Room temperature | Overnight | 56.0 | 17,200 |
| Example 14 | EC | Au | $TiO_2$ | 1:25 | Room temperature | Overnight | 40.8 | 34,900 |
| Example 15 | EGC | Au | $TiO_2$ | 1:25 | Room temperature | Overnight | 49.6 | 18,100 |
| Example 16 | ECg | Au | $TiO_2$ | 1:25 | Room temperature | Overnight | 62.1 | 53,700 |
| Example 17 | EGCg | Au | $TiO_2$ | 1:25 | Room temperature | Overnight | 75.0 | 43,800 |
| Example 18 | C | Au | $TiO_2$ | 1:25 | Room temperature | Overnight | 43.1 | 9,880 |
| Example 19 | EGCg | Au | $TiO_2$ | 1:5.2 | 60° C. | 0.5 h | 32.9 | 12,400 |
| Example 20 | EGCg | Au | $TiO_2$ | 1:5.2 | 60° C. | 1 h | 36.0 | 11,600 |
| Example 21 | EGCg | Au | $TiO_2$ | 1:5.2 | 60° C. | 24 h | 68.1 | 48,300 |
| Example 22 | EGCg | Au | $TiO_2$ | 1:10.4 | 60° C. | 0.5 h | 51.3 | 16,100 |
| Example 23 | EGCg | Au | $TiO_2$ | 1:2.6 | 60° C. | 1 h | 25.5 | 12,200 |
| Comparative Example 1 | EC + EGC | | $SiO_2$ | 1:25 | Room temperature | Overnight | 11.5 | 4,840 |
| Comparative Example 2 | EC + EGC | None | | 1:25 | Room temperature | Overnight | 11.4 | 7,750 |
| Comparative Example 3 | EGCg | Au | $TiO_2$ | — | 60° C. | 1 h | 10.1 | 8,060 |

As described hereinbefore, by using the production method of the present invention, polyphenol can be easily synthesized.

The invention claimed is:

1. A method for producing polyphenol comprising allowing catechins to react in the presence of an oxidizing agent and a catalyst to thereby produce the polyphenol, wherein the catalyst comprises
   a metal oxide, and/or
   a composite comprising a substrate having a surface comprising an inorganic material and metal nanoparticles adhered to a surface of the inorganic material and having a particle diameter of not less than 0.5 nm and not more than 100 nm,
   wherein in the reaction, a molar ratio between the catechins and the oxidizing agent is 1:1 to 1:50,
   a concentration of the catechins is 6.4 mM or more, and
   a number-average molecular weight of the polyphenol is not less than 9,000 and not more than 18,000.

2. The method for producing polyphenol according to claim 1, wherein the catalyst comprises the composite, and the metal nanoparticles are one or more selected from the group consisting of Au, Pd, Pt, Rh, Ru, Ir, Ag, and oxides thereof.

3. The method for producing polyphenol according to claim 1, wherein the catalyst comprises the composite comprising the metal nanoparticles adhered to a surface of one or more inorganic materials selected from the group consisting of $SiO_2$, $ZrO_2$, $Fe_2O_3$, $Al_2O_3$, C and $TiO_2$.

4. The method for producing polyphenol according to claim 1, wherein the catalyst comprises one or more metal oxides selected from the group consisting of $WO_3$, $Fe_2O_3$, $Ag_2O$ and CuO.

5. The method for producing polyphenol according to claim 1, wherein the oxidizing agent is hydrogen peroxide or oxygen.

6. The method for producing polyphenol according to claim 1, wherein the reaction is carried out in a solvent and is carried out at a temperature of not lower than 15° C. and not higher than the boiling point of the solvent.

7. The method for producing polyphenol according to claim 6, wherein the solvent is water.

8. A method for producing polyphenol comprising allowing catechins to react in the presence of an oxidizing agent and a catalyst to thereby produce the polyphenol, wherein the catalyst comprises
   a metal oxide, and/or
   a composite comprising a substrate having a surface comprising an inorganic material and metal nanoparticles adhered to a surface of the inorganic material and having a particle diameter of not less than 0.5 nm and not more than 100 nm, and
   wherein a number-average molecular weight of the polyphenol is not less than 9,000 and not more than 18,000.

9. The method for producing polyphenol according to claim 8, wherein the catalyst comprises the composite, and the metal nanoparticles are one or more selected from the group consisting of Au, Pd, Pt, Rh, Ru, Ir, Ag, and oxides thereof.

10. The method for producing polyphenol according to claim 8, wherein the catalyst comprises the composite comprising the metal nanoparticles adhered to a surface of one or more inorganic materials selected from the group consisting of $SiO_2$, $ZrO_2$, $Fe_2O_3$, $Al_2O_3$, C and $TiO_2$.

11. The method for producing polyphenol according to claim 8, wherein the catalyst comprises one or more metal oxides selected from the group consisting of $WO_3$, $Fe_2O_3$, $Ag_2O$ and CuO.

12. The method for producing polyphenol according to claim 8, wherein the oxidizing agent is hydrogen peroxide or oxygen.

13. The method for producing polyphenol according to claim 8, wherein in the reaction, a molar ratio between the catechin and the oxidizing agent is 1:1 to 1:50.

14. The method for producing polyphenol according to claim 8, wherein the reaction is carried out in a solvent and is carried out at a temperature of not lower than 15° C. and not higher than the boiling point of the solvent.

15. The method for producing polyphenol according to claim 14, wherein the solvent is water.

16. A method for producing polyphenol comprising allowing catechins to react in the presence of an oxidizing agent and a catalyst to thereby produce the polyphenol, wherein the catalyst comprises
   a metal oxide, and/or
   a composite comprising a substrate having a surface comprising an inorganic material and metal nanoparticles adhered to a surface of the inorganic material and having a particle diameter of not less than 0.5 nm and not more than 100 nm, and
wherein the oxidizing agent is hydrogen peroxide.

* * * * *